(12) United States Patent
Kim et al.

(10) Patent No.: US 11,385,220 B2
(45) Date of Patent: Jul. 12, 2022

(54) METHODS FOR MEASURING OXIDATIVE STRESS IN HUMAN BODY FLUIDS

(71) Applicant: CHUNGDO PHARM. CO., LTD, Chuncheon-si (KR)

(72) Inventors: Sung-Jin Kim, Seoul (KR); Sung-Jae Lee, Chuncheon-si (KR); Abeje Abebayehu Silte, Chuncheon-si (KR)

(73) Assignee: CHUNGDO PHARM. CO., LTD, Chuncheon-si (KR)

( * ) Notice: Subject to any disclaimer, the term of this patent is extended or adjusted under 35 U.S.C. 154(b) by 639 days.

(21) Appl. No.: 16/342,054

(22) PCT Filed: May 11, 2018

(86) PCT No.: PCT/KR2018/005413
§ 371 (c)(1),
(2) Date: Apr. 15, 2019

(87) PCT Pub. No.: WO2018/230842
PCT Pub. Date: Dec. 20, 2018

(65) Prior Publication Data
US 2019/0234932 A1  Aug. 1, 2019

(30) Foreign Application Priority Data

Jun. 14, 2017  (KR) .......................... 10-2017-0074738

(51) Int. Cl.
| | |
|---|---|
| *G01N 33/493* | (2006.01) |
| *G01N 21/78* | (2006.01) |
| *G01N 33/49* | (2006.01) |
| *G01N 33/52* | (2006.01) |
| *G01N 33/53* | (2006.01) |
| *G01N 33/58* | (2006.01) |
| *G01N 33/92* | (2006.01) |
| *G01N 33/72* | (2006.01) |

(52) U.S. Cl.
CPC ........... *G01N 33/493* (2013.01); *G01N 21/78* (2013.01); *G01N 33/49* (2013.01); *G01N 33/52* (2013.01); *G01N 33/5308* (2013.01); *G01N 33/583* (2013.01); *G01N 33/721* (2013.01); *G01N 33/92* (2013.01); *G01N 2800/7009* (2013.01)

(58) Field of Classification Search
None
See application file for complete search history.

(56) References Cited

U.S. PATENT DOCUMENTS

| 3,359,072 A | 12/1967 | Rey et al. |
|---|---|---|
| 6,165,797 A | 12/2000 | Halstead |

FOREIGN PATENT DOCUMENTS

| CN | 104024852 A | 9/2014 |
|---|---|---|
| KR | 1997-0001814 B1 | 2/1997 |
| KR | 10-2002-0031673 A | 5/2002 |
| KR | 10-2002-0094899 A | 12/2002 |
| KR | 10-2007-0073918 A | 7/2007 |
| KR | 10-2013-0088623 A | 8/2013 |
| KR | 10-1669918 B1 | 10/2016 |

OTHER PUBLICATIONS

Malonic Acid information Sheets, 2012 WikiDoc (https://www.wikidoc.org/index.php/Malonic_acid) (retrieved from the internet on Jan. 10, 2022). (Year: 2012).*
Feldman; Thiobarbituric acid reactive susbatances (TBARS) Assay; AMDCC Protocols Journal; Aug. 2004; pp. 1-3; vol. 1.
Skoza et al., "Stable Thiobarbituric Acid Chromophore with Dimethyl Sulphoxide. Application To Sialic Acid Assay in Analytical De-O-Acetylation", Biochem. J., 1976, vol. 159, pp. 457-462 (6 pages total).

* cited by examiner

*Primary Examiner* — Marsha Tsay
(74) *Attorney, Agent, or Firm* — Sughrue Mion, PLLC

(57) ABSTRACT

Provided is, as an attempt to realize a method for measuring oxidative stress in human body fluids, a means for measuring reactive oxygen species containing a color indicator that detects the amount of reactive oxygen species present in the human body by causing a color change through reaction with malondialdehyde present in the urine or blood. The detection means has advantages of detecting malondialdehyde (MDA) present at a low concentration in a sample (urine or blood) and exhibiting excellent discrimination owing to high detection sensitivity.

6 Claims, 3 Drawing Sheets

METHODS FOR MEASURING OXIDATIVE STRESS IN HUMAN BODY FLUIDS

TECHNICAL FIELD

The present invention relates to, as a method for measuring oxidative stress in human body fluids, a means for measuring reactive oxygen species containing a color indicator that detects the amount of reactive oxygen species present in the human body by causing a color change through reaction with malondialdehyde present in the urine and blood.

BACKGROUND ART

In the metabolic process of oxygen in the human body, free radicals called "reactive oxygen species (active oxygen)" are generated as reaction byproducts. Reactive oxygen species have been reported to have negative effects on the human body, and a typical negative effect thereof is production of lipid peroxides in human tissues. Lipid peroxidation means oxidative damage of unsaturated lipids. Free radicals, which are reactive oxygen species, oxidize phospholipids in cell membranes containing large amounts of unsaturated fatty acids to accumulate lipid peroxides in the cell membranes. Thus, the increase of reactive oxygen species in the human body facilitates the production of lipid peroxides, and the lipid peroxides ultimately cause a variety of human diseases such as stroke and myocardial infarction.

Therefore, it is very important to measure the amount of reactive oxygen species in the human body for prophylactic or diagnostic purpose. It is difficult to directly measure reactive oxygen species due to high reactivity. Therefore, as an alternative thereto, the amount of lipid peroxide generated by reactive oxygen species is detected and is often used as an index for the amount of reactive oxygen species.

Malondialdehyde (MDA) is an indicator of the degree of lipid peroxidation. MDA can be easily detected in the blood or urine, can be converted to the degree of lipid peroxidation and also enables the amount of reactive oxygen species in the human body to be detected.

HLPC and thiobarbituric acid reactant substrate (TBARS) methods have been widely known as conventional methods for measuring malondialdehyde. However, these methods have disadvantages in that they are difficult for the general public to practice because they require separate apparatuses and expertise. At present, public interest in reactive oxygen species has increased, so members of the public want to be able to easily detect their own oxidative stress. Therefore, there is a need for the development of methods for measuring malondialdehyde in a simple manner, and a strip-shaped detection means may be a potent alternative thereto.

DISCLOSURE

Technical Problem

Therefore, the present invention has been made in view of the above problems, and it is an object of the present invention to develop and provide a detection means that is capable of detecting malondialdehyde (MDA), which serves as an index of detection of the amount of reactive oxygen species in the human body, in spite of being present at a low concentration in a sample (urine or blood), and exhibiting excellent discrimination owing to high detection sensitivity.

Technical Solution

In accordance with the present invention, the above and other objects can be accomplished by the provision of a color indicator for detecting the amount of reactive oxygen species present in a human body by causing a color change through reaction with malondialdehyde (MDA) present in the urine or blood, wherein the color indicator is 1,3-diethyl-2-thiobarbituric acid (TBA) dissolved in ethanol, an aqueous ethanol solution or purified water, each supplemented with dimethyl sulfoxide (DMSO).

In the color indicator of the present invention, the dimethyl sulfoxide (DMSO) is preferably added in an amount of 5 to 30 parts by weight to 100 parts by weight of the ethanol, aqueous ethanol solution, or purified water.

In the present invention, TBA is used in such a manner that it is dissolved in ethanol, an aqueous ethanol solution, or purified water. In this case, the present invention is characterized in that DMSO is added to the ethanol, aqueous ethanol solution, or purified water. The reason for this is to improve the solubility of TBA.

Meanwhile, it is preferable that the color indicator according to the present invention contains an organic acid and a conjugate base thereof as buffers against a sudden pH change. In addition, preferably, the organic acid is malonic acid, and the conjugate base to the organic acid is diethyl malonate. In addition, preferably, the malonic acid is added in an amount of 10 to 30 parts by weight to 100 parts by weight of ethanol, or an aqueous ethanol solution or purified water, and the diethyl malonate is added in an amount of 5 to 25 parts by weight to 100 parts by weight of ethanol, or an aqueous ethanol solution or purified water.

By using malonic acid and diethyl malonate as buffers, the detection sensitivity of malondialdehyde can be improved even at a low concentration.

Meanwhile, the color indicator according to the present invention or a solution containing the same may further contain a surfactant and a stabilizer, in addition to the above-mentioned buffer solution.

The surfactant may serve to uniformly maintain the color change of the color indicator in the detection means (for example, the test paper). For example, the surfactant is sodium dodecyl sulfate (SDS), dodecylbenzenesulfonic acid (DBS), dioctyl sulfosuccinate, or the like.

The stabilizer enables the color indicator (e.g., test paper) to be uniformly fixed at the detection means. For example, polymers soluble in ethanol, an aqueous ethanol solution or purified water can be used. A more specific example thereof is hydroxy cyclodextrin.

The present invention also provides a means for measuring reactive oxygen species in the human body containing a color indicator that detects the amount of reactive oxygen species present in the human body by causing a color change through reaction with malondialdehyde present in the urine or blood, wherein the color indicator is 1,3-diethyl-2-thiobarbituric acid (TBA) dissolved in ethanol, an aqueous ethanol solution or purified water, each supplemented with dimethyl sulfoxide (DMSO).

In the means for measuring reactive oxygen species in the human body according to the present invention, it is preferable that an organic acid and a conjugate base thereof be dissolved as buffers against a sudden pH change in the ethanol, aqueous ethanol solution or purified water. In addition, the organic acid is preferably malonic acid, and the conjugate base to the organic acid is preferably diethyl malonate.

In the means for measuring reactive oxygen species in a human body according to the present invention, the color indicator is preferably absorbed in a liquid state in the means for measuring reactive oxygen species in the human body, and then dried.

In the means for measuring reactive oxygen species in the human body according to the present invention, the measuring means may be, for example, any one selected from paper, a nonwoven fabric and a woven fabric.

The production process of the means for measuring reactive oxygen species in the human body will be briefly described. For example, TBA is dissolved in a solvent (ethanol, an aqueous ethanol solution or purified water), and a substrate (for example, paper, a nonwoven fabric or a woven fabric) is immersed in the resulting solution, followed by drying. In this case, preferably, the means for measuring reactive oxygen species is produced by further dissolving a buffer solution, a stabilizer and a surfactant in a solvent and then drying the resulting solution.

Advantageous Effects

The means for measuring reactive oxygen species in a human body according to the present invention has advantages of detecting malondialdehyde (MDA) present at a low concentration in a sample (urine or blood) and exhibiting excellent discrimination owing to high detection sensitivity.

BRIEF DESCRIPTION OF THE DRAWINGS

The above and other objects, features and other advantages of the present invention will be more clearly understood from the following detailed description taken in conjunction with the accompanying drawings, in which.

BEST MODE

Figure 1:
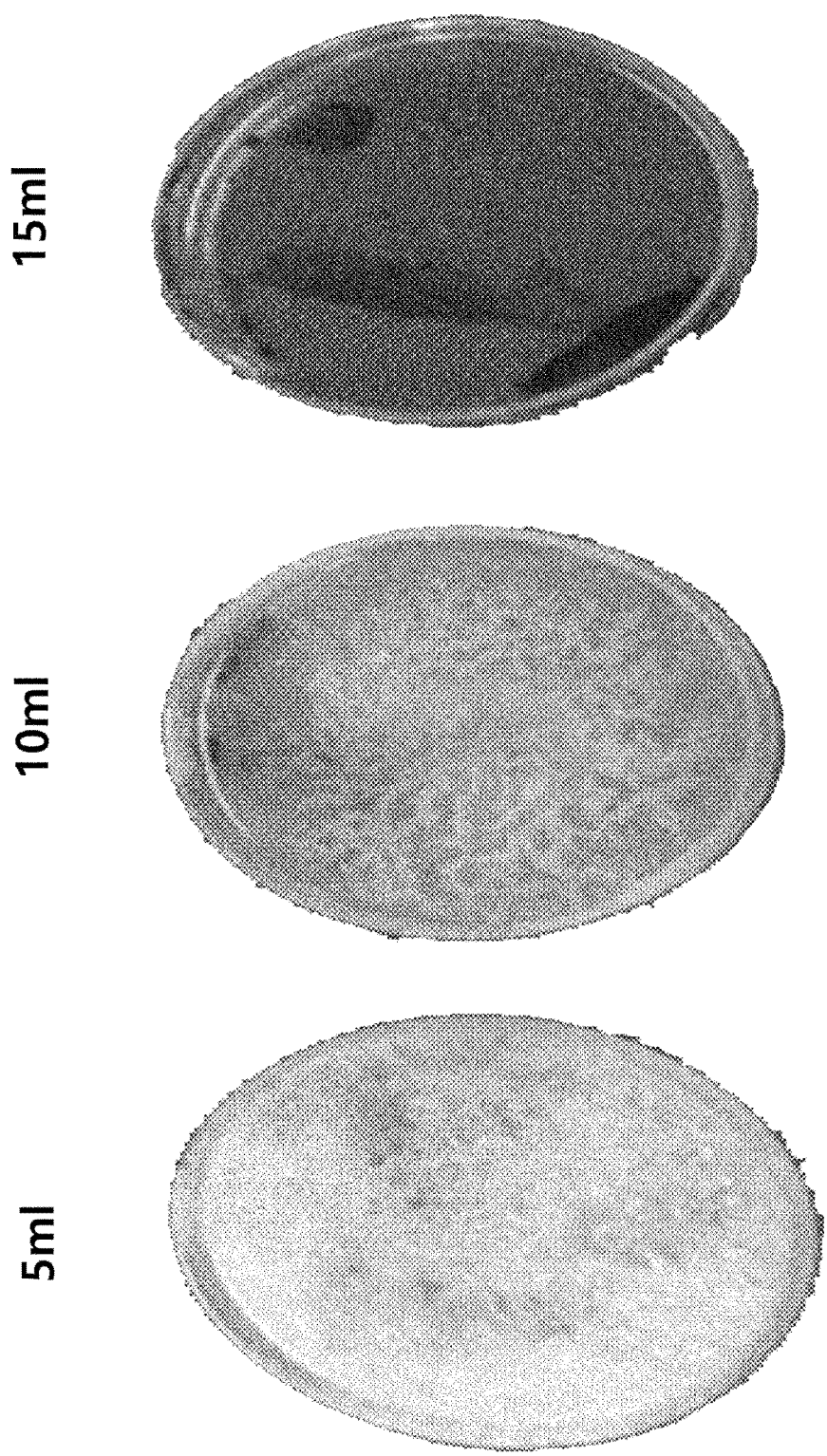
FIG. 1 is an image showing crystallization of a solution containing TBA (color indicator) depending on the amount of DMSO added.

In the present invention, 1,3-diethyl-2-thiobarbituric acid (TBA) is used as a color indicator (also called "color development indicator) for the detection of malondialdehyde (MDA) present in the urine.

In the prior art (Korean Patent Laid-open No. 10-2013-0088623), the amount of TBA added was only 2 to 3%. This is due to the problem that TBA is not dissolved in distilled water and only about 3.5% thereof is dissolved in ethanol.

The amount of TBA added may affect the measurement sensitivity of malondialdehyde. As the amount of TBA added increases, MDA can be detected in a low concentration and MDA detection can thus be improved. Strips were actually produced and inspected according to the method disclosed in the prior art of Korean Patent Laid-open No. 10-2013-0088623. In this case, the discrimination ability was low at an MDA concentration of 1 mM or less.

Since the concentration of MDA in the human body as well as urine is as high as 1 mM or less, a MDA detection means should be designed to detect 1 mM or less of MDA. However, the method according to the published patent is unable to detect 1 mM or less of MDA.

The present invention was made in consideration of two approaches in order to overcome the aforementioned drawbacks. One is to increase the solubility of TBA and the other is to control a reaction acidity to be better through an organic acid.

In the conventional published Patent No. 10-2013-0088623, the addition of 2 to 3 parts by weight of 1,3-diethyl-2-thiobarbituric acid (TBA) was determined to be an appropriate concentration with respect to 100 parts by weight of distilled water due to the solubility problem of TBA thereof. However, in the present invention, the solubility problem of TBA is solved by adding DMSO. By adding DMSO, 3.5 parts or more by weight of TBA can be dissolved in 100 parts by weight of distilled water or ethanol.

In addition, in the conventional published patent No. 10-2013-0088623, the increase in color development is insufficient when TBA is present in an amount of 3 parts by weight or more. However, the addition of DMSO causes an increase in color development with an increase in amount of TBA, even when 3 parts by weight or more of TBA are added. This means that color discrimination at a low concentration becomes clearer, which enables accurate examination.

Meanwhile, in the conventional published Patent No. 10-2013-0088623, a buffer solution was prepared by mixing 10 to 30 parts by weight of citric acid and 20 to 30 parts by weight of trisodium citrate with 100 parts by weight of distilled water. However, since the buffer solution has a small electron emission, the reaction rate is inevitably low.

Therefore, in the present invention, it was determined that an organic acid emitting a larger amount of electrons would be required, and malonic acid was selected as an organic acid capable of maintaining the stability of the strip among buffer solutions emitting a larger amount of electrons. Also, diethyl malonate was selected as a conjugate base of malonic acid.

Thus, it was found that, when malonic acid was selected as the organic acid and diethyl malonate was selected as a conjugate base thereof, the sensitivity was improved at a lower concentration than when citric acid was used. When 10 to 30 parts by weight of malonic acid and 5 to 25 parts by weight of diethyl malonate were added to 100 parts by weight of a solvent (water, ethanol or an aqueous ethanol solution), the pH was maintained at about 1 to 4 and the reactivity was the best.

Hereinafter, the present invention will be described in more detail with reference to the following examples. The scope of the present invention is not limited to these examples and includes technical concepts equivalent thereto as well.

Example 1: Use of TBA Dissolved in DMSO

In the present example, DMSO (dimethyl sulfoxide) was added to the TBA solution. It was found that, when DMSO was added, the solubility of TBA was increased. DMSO is an important solvent that dissolves both polar and nonpolar compounds, and can be used in combination with various organic solvents as well as water.

It was difficult to dissolve TBA in an amount of 3.5 parts by weight or more based on 100 parts by weight of the solvent in accordance with the method of the conventional art disclosed in published Patent No. 10-2013-0088623, and although dissolved, TBA was precipitated during the process. However, it was found that, when DMSO was added, TBA could be dissolved in up to 5 parts by weight with respect to 100 parts by weight of the solvent, and that better sensitivity was obtained at 1 mM or less.

FIG. 1 is an image showing crystallization of a solution containing TBA as a color indicator depending on the amount of DMSO added. It was found that, when a test paper was immersed in the TBA-containing solution and then allowed to stand at room temperature for the same time, as the amount of DMSO added to the solution increased, TBA recrystallization decreased.

Figure 2:
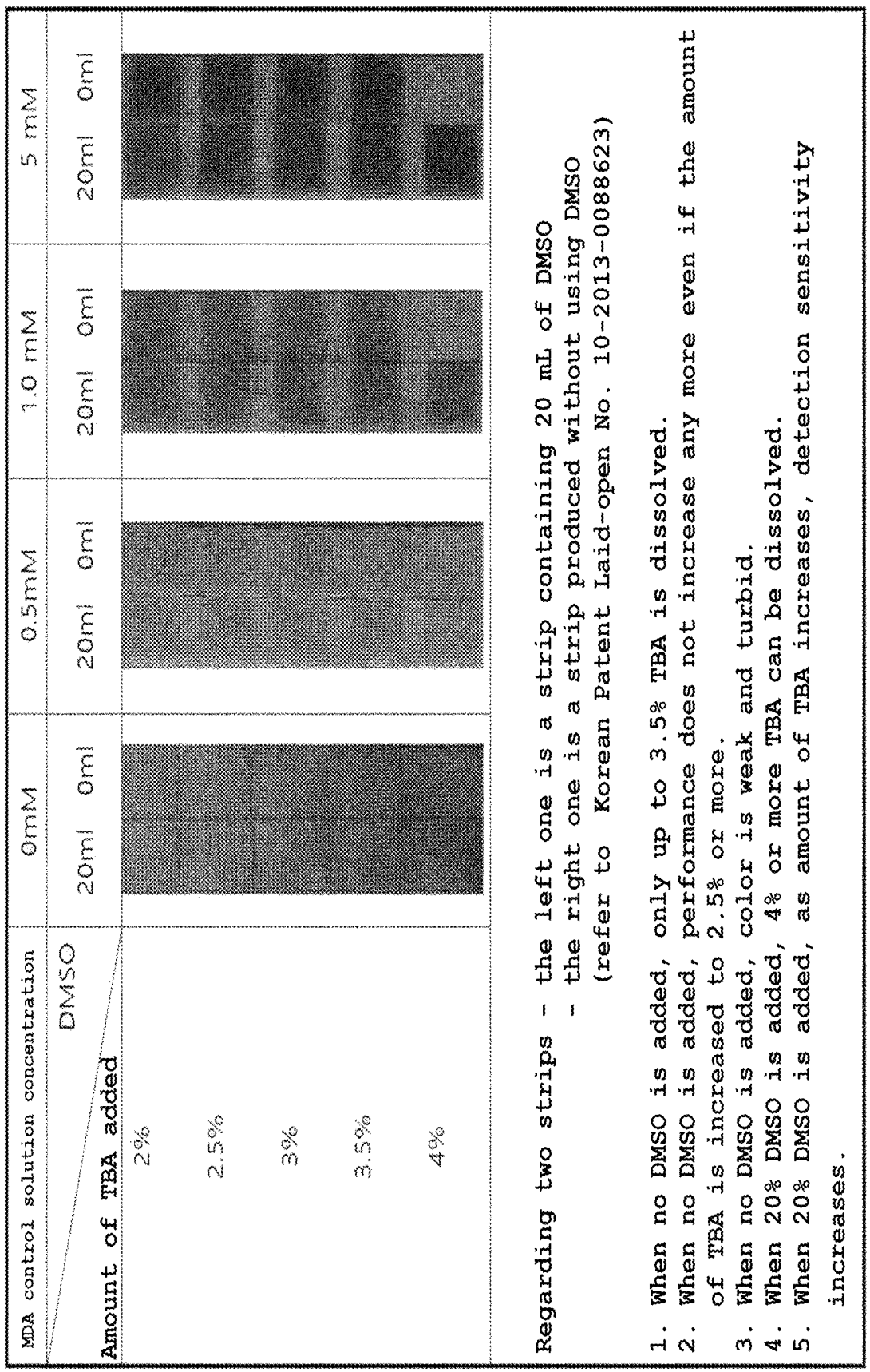
FIG. 2 is an image comparing the amount of TBA (color indicator) added and color development change depending on whether or not DMSO is added.

In addition, when TBA was added and dissolved alone, rough purple was obtained, whereas, when TBA was dissolved by adding DMSO, it was found that red was more clearly shown, even if the same amount was added (FIG. 2). FIG. 2 is an image comparing the amount of TBA added and the color development change depending on whether or not DMSO was added.

Meanwhile, DMSO is preferably added in an amount of 5 to 30 parts by weight, and it is not preferable to add DMSO in an amount exceeding the range, because this may affect stability.

Example 2: Improvement of Reactivity Due to Use of Malonic Acid

In the present example, the reactivity could be improved by controlling reaction acidity using malonic acid.

Korean Patent Laid-Open No. 10-2013-0088623 discloses the production of strips using a mixture of 10 to 30 parts by weight of citric acid and 20 to 30 parts by weight of trisodium citrate as reaction buffers against a sudden pH change.

Since citric acid is a weak acid, it helps to maintain the stability of the strip. However, since it slowly releases $H^+$ during reaction of MDA with TBA, the reaction is inevitably slow and weak.

Thus, in the present embodiment, experiments satisfying acidic conditions were conducted using various organic acids. When a variety of acids in addition to citric acid were used to maintain a pH of 2 to 4, the reactivity of the color reaction between TBA and MDA increased, but stability tended to decrease.

Figure 3:
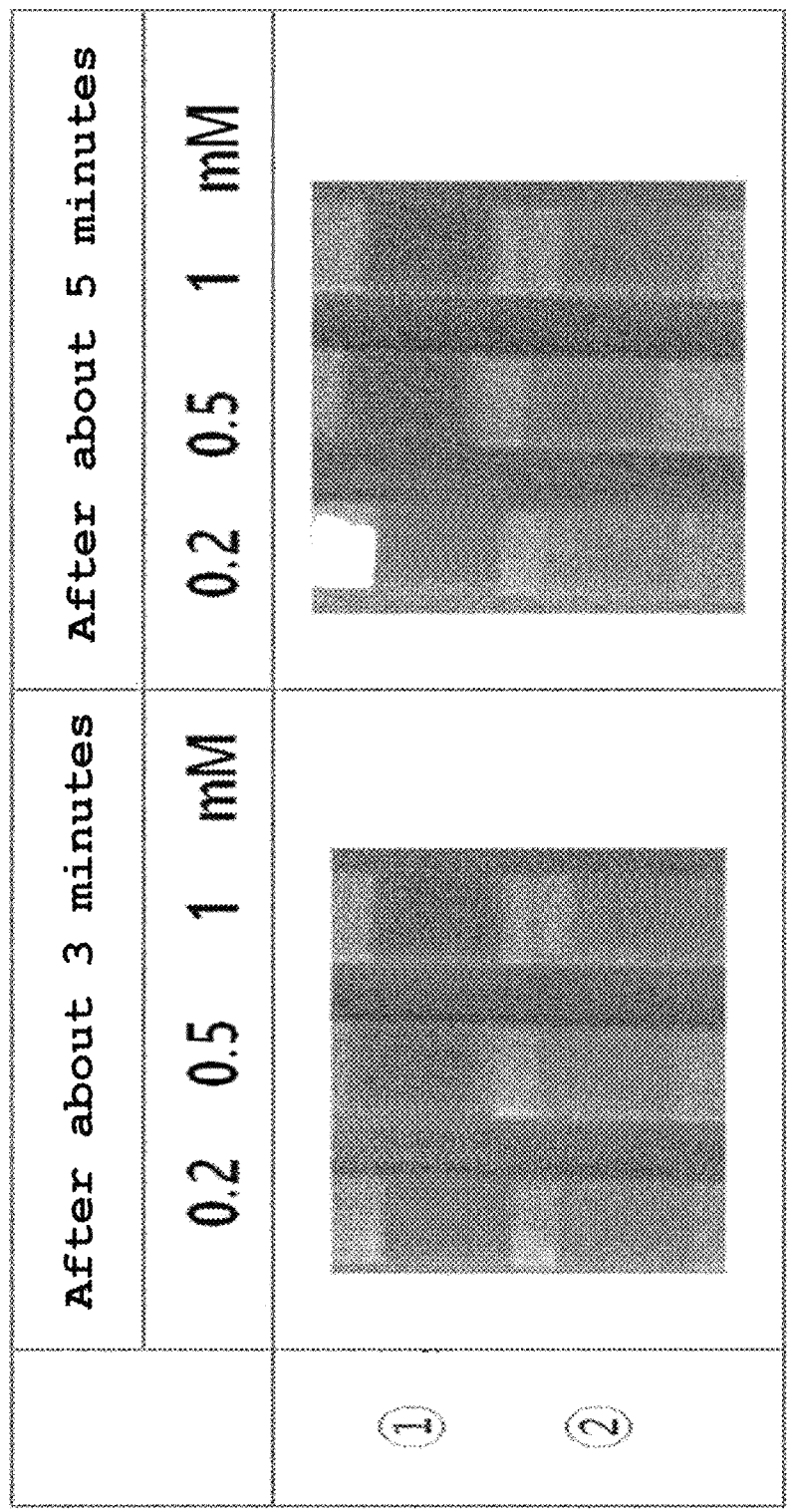
FIG. 3 is an image showing the reaction rate and the degree of color development of a strip using malonic acid and DMSO according to the present invention, compared to a conventional strip using citric acid.

In the present invention, malonic acid was discovered as an organic acid capable of improving both the stability of the strip and the reactivity of TBA and MDA. It was also found that, when diethyl malonate was used as a conjugate base of malonic acid, sensitivity was improved at a lower concentration than when citric acid was used (FIG. 3). FIG. 3 is an image showing the reaction rate and the degree of color development of a strip using malonic acid and DMSO according to the present invention as compared to a conventional strip using citric acid. FIG. 3 shows the result of an experiment including the addition of malonic acid and diethyl malonate to distilled water, and the addition of citric acid to distilled water as a control group. Further, 0.2. 0.5 and 1 mM in FIG. 3 means the concentration of malondialdehyde as a subject to be detected.

From the aforementioned experiments, it could be seen that when 10 to 30 parts by weight of malonic acid and 5 to 25 parts by weight of diethyl malonate are added to 100 parts by weight of the solvent, the pH was maintained at about 1 to 4 and the reactivity is the best. When the pH is low, the reaction rate and the color difference in the early stage of the reaction are improved. On the other hand, when the pH is high, the initial reaction rate is slow, but the distinction between the concentrations becomes clear over time.

What is claimed:

1. A color indicator composition for detecting an amount of reactive oxygen species present in a human body by causing a color change through reaction with malondialdehyde (MDA) present in urine or blood, comprising:
   1,3-diethyl-2-thiobarbituric acid (TBA) dissolved in ethanol, an aqueous ethanol solution or purified water, each supplemented with dimethyl sulfoxide (DMSO), and
   an organic acid and a conjugate base thereof, as a buffer against a sudden pH change, wherein the organic acid is malonic acid and the conjugate base to the organic acid is diethyl malonate,
   wherein the dimethyl sulfoxide (DMSO) is added in an amount of 5 to 30 parts by weight to 100 parts by weight of the ethanol, aqueous ethanol solution, or purified water.

2. The color indicator composition according to claim 1, wherein the malonic acid is added in an amount of 10 to 30 parts by weight to 100 parts by weight of the ethanol, aqueous ethanol solution, or purified water, and the diethyl malonate is added in an amount of 5 to 25 parts by weight to 100 parts by weight of the ethanol, aqueous ethanol solution, or purified water.

3. A substrate for measuring reactive oxygen species in a human body comprising a color indicator that detects an amount of reactive oxygen species present in a human body by causing a color change through reaction with malondialdehyde present in urine or blood,
   wherein the color indicator is 1,3-diethyl-2-thiobarbituric acid (TBA) dissolved in ethanol, an aqueous ethanol solution or purified water, each supplemented with dimethyl sulfoxide (DMSO),
   wherein an organic acid and a conjugate base thereof are dissolved as a buffer against a sudden pH change in the ethanol, aqueous ethanol solution or purified water,
   wherein the organic acid is malonic acid and the conjugate base to the organic acid is diethyl malonate,
   wherein the dimethyl sulfoxide (DMSO) is added in an amount of 5 to 30 parts by weight to 100 parts by weight of the ethanol, aqueous ethanol solution, or purified water.

4. The substrate for measuring reactive oxygen species according to claim 3, wherein the color indicator is absorbed in a liquid state in the substrate for measuring reactive oxygen species in a human body and is then dried.

5. The substrate for measuring reactive oxygen species according to claim 3, wherein the substrate is selected from paper, a nonwoven fabric and a woven fabric.

6. A method for measuring reactive oxygen species in a subject in need thereof, comprising contacting a biological sample obtained from the subject with the color indicator composition of claim 1.

* * * * *